Figure 1:
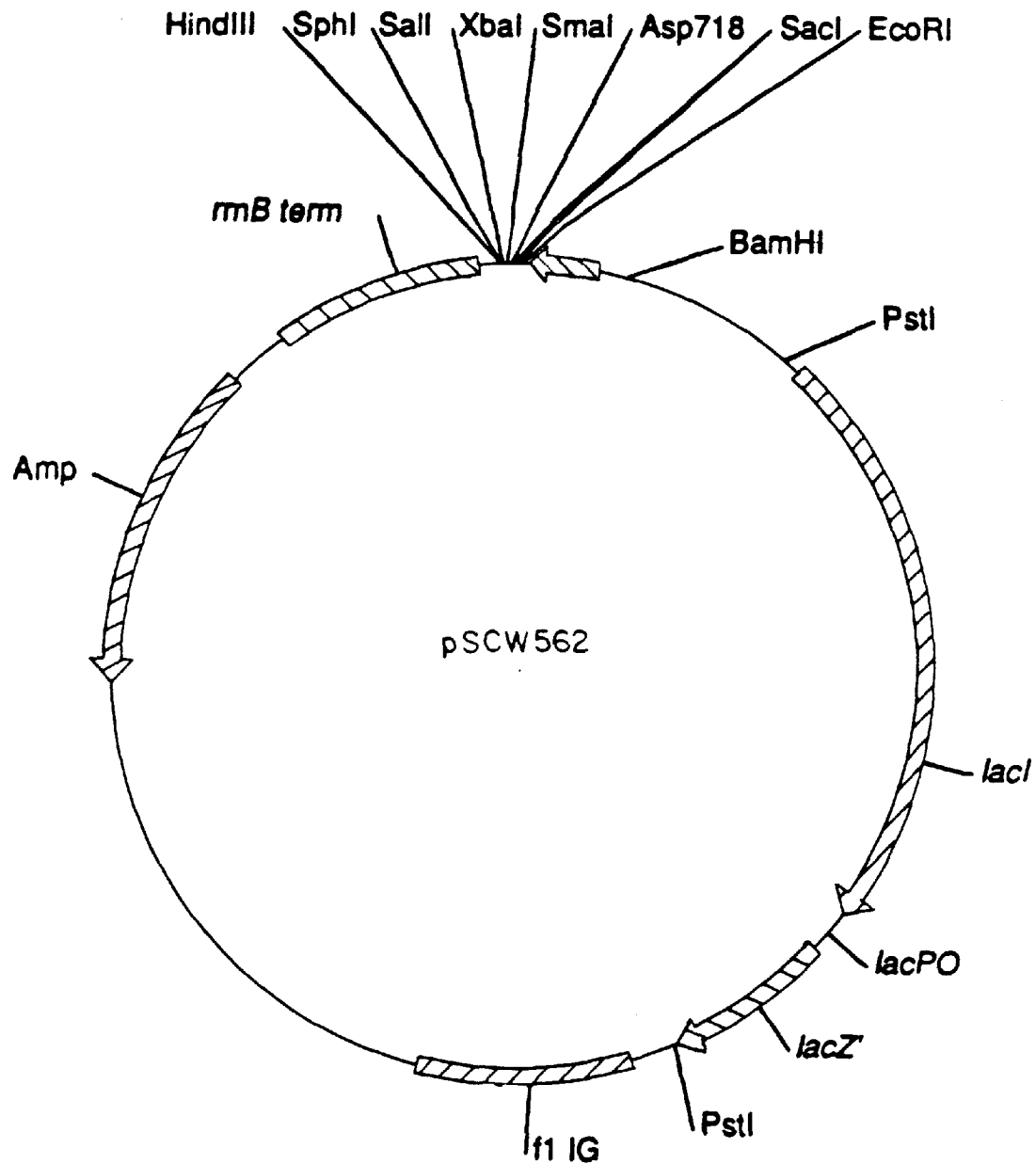

United States Patent
Sullivan

Patent Number: 6,083,686
Date of Patent: Jul. 4, 2000

[54] **INCREASED PRODUCTION OF *THERMUS AQUATICUS* DNA POLYMERASE IN *E. COLI***

[75] Inventor: Mark A. Sullivan, Rochester, N.Y.

[73] Assignee: Johnson & Johnson Clinical Diagnostic Systems, Inc., Rochester, N.Y.

[21] Appl. No.: 07/602,848

[22] Filed: Oct. 26, 1990

[51] Int. Cl.⁷ .............. C12Q 1/68; C12N 1/21; C12N 15/11; C12N 15/63

[52] U.S. Cl. .......... 435/6; 435/252.33; 435/91.4; 435/91.42; 435/69.1; 435/69.7; 435/320.1; 536/23.1; 536/23.2

[58] Field of Search ............... 435/69.1, 172.3, 435/232, 252.33, 320.1, 69.7, 471, 91.2, 6, 91.4, 91.42; 536/27, 23.1, 23.2

[56] References Cited

U.S. PATENT DOCUMENTS

| | | | |
|---|---|---|---|
| 4,703,004 | 10/1987 | Hopp et al. | 435/69.7 |
| 4,782,137 | 11/1988 | Hopp et al. | 530/328 |
| 4,889,818 | 12/1989 | Gelfand et al. | 435/194 |

FOREIGN PATENT DOCUMENTS

| | | |
|---|---|---|
| 89/03886 | 5/1989 | WIPO. |
| 89-06691 | 7/1989 | WIPO. |

OTHER PUBLICATIONS

Saiki et al. (1988), Science 239: 487–491.
Grosjean et al. (1982), Gene 18: 199–209.
Gerard et al., Biochemistry (1990), vol. 29, pp. 9274–9281. Construction and Expression of a Novel Recombinant Anaphylatoxin, C5a–N19, as a Probe for the Human C5a Receptor.
Hopp et al., Bio/Technology (1988), vol. 6, pp. 1204–1210. A short Polypeptide Marker Sequence Useful For Recombinant Protein Identification and Purification.
Bonekamp et al., Nucleic Acids Research (1988), vol. 16, No. 7. The AGG codon is translated slowly in *E.coli* even at very low expression levels.
Lee et al., Gene (1987), vol. 58, pp. 77–86. Modification of mRNA secondary structure and alteration of the expression of human interferon α1 in *Escherichia coli*.
Lawyer et al., (1989), Journal of Biological Chemistry, vol., 264, No. 11, Issue of Apr. 15, pp. 6427–6437. Isolation, Characterization, and Expression in *Escherichia coli* of the DNA Polymerase Gene from *Thermus aquaticus*.
Pricket et al., (1989), BioTechniques, vol. 7, No. 6. A Calcium–Dependent Antibody for Identification and Purification of Recombinant Proteins.
Isacchi, A. et al, (1989), Mature Apolipoprotein A1 and its Precursor, proApoA1: Influence of the Sequence at the 5' end of the Gene on the Efficiency of Expression in *Escherichia coli.*, Gene 81:129–137.
Looman, A. C. et al., (1987), Influence of the Codon Following the AUG Initiation Codon on the Expression of a Modified lacZ Gene in *Escherichia coli.*, EMBO Journal 6:2489–2492.
Hsiung, H. M. et al, (1987), Expression of Bovine Growth Hormone Derivatives in *Escherichia coli* and the Use of the Derivatives to Produce Natural Sequence Growth Hormone by Cathepsin C Cleavage, Methods Enzymol. 153:390–401.

*Primary Examiner*—David Guzo
*Assistant Examiner*—John Shuman

[57] ABSTRACT

The *Thermus aquaticus* gene encoding a thermostable DNA polymerase (Taq Pol) is altered in the N-terminus-encoding region to provide mutant genes with improved expression in *E. coli*.

9 Claims, 1 Drawing Sheet

```
                         SEQUENCE LISTING (1) GENERAL INFORMATION:

(iii) NUMBER OF SEQUENCES:  14

(2) INFORMATION FOR SEQ ID NO:1:

(i) SEQUENCE CHARACTERISTICS:
          (A) LENGTH:  2499

(B) TYPE:  nucleic acid (C) STRANDEDNESS:  double (D) TOPOLOGY:  linear (ii) MOLECULE TYPE:  genomic DNA (iii) HYPOTHETICAL:  no (iv) ANTI-SENSE:  no (vi) ORIGINAL SOURCE:
          (A) ORGANISM:  Thermus aquaticus (B) INDIVIDUAL ISOLATE:  YT1, ATCC 25104

(vii) IMMEDIATE SOURCE:  amplified from genomic DNA (ix) FEATURE:
          (A) NAME/KEY:  peptide (B) LOCATION:  1-2496

(C) IDENTIFICATION METHOD:  comparison to sequence in GenBank, Accession number J04639.

(x) PUBLICATION INFORMATION:
          (A) AUTHORS:  Lawyer, F.C., Stoffel, S.,

Saiki, R.K., Myambo, K., Drummond, R.,
                Gelfand, D.H.
          (B) TITLE:  Isolation, characterization and expression in Escherichia coli of the DNA
                polymerase gene from Thermus aquaticus.
          (C) JOURNAL:  Journal of Biological Chemistry
          (D) VOLUME:  264

(E) ISSUE:  11

(F) PAGES:  6427-6437

(G) DATE:  15 April 1989

(xi) SEQUENCE DESCRIPTION:  SEQ ID NO:1:

ATG AGG GGG ATG CTG CCC CTC TTT GAG CCC AAG GGC CGG GTC CTC        45
Met Arg Gly Met Leu Pro Leu Phe Glu Pro Lys Gly Arg Val Leu
1               5                  10                 15

CTG GTG GAC GGC CAC CAC CTG GCC TAC CGC ACC TTC CAC GCC CTG        90
Leu Val Asp Gly His His Leu Ala Tyr Arg Thr Phe His Ala Leu
                20                  25                 30
```

-continued

```
AAG GGC CTC ACC ACC AGC CGG GGG GAG CCG GTG CAG GCG GTC TAC        135
Lys Gly Leu Thr Thr Ser Arg Gly Glu Pro Val Gln Ala Val Tyr
             35                  40                  45

GGC TTC GCC AAG AGC CTC CTC AAG GCC CTC AAG GAG GAC GGG GAC        180
Gly Phe Ala Lys Ser Leu Leu Lys Ala Leu Lys Glu Asp Gly Asp
             50                  55                  60

GCG GTG ATC GTG GTC TTT GAC GCC AAG GCC CCC TCC TTC CGC CAC        225
Ala Val Ile Val Val Phe Asp Ala Lys Ala Pro Ser Phe Arg His
             65                  70                  75

GAG GCC TAC GGG GGG TAC AAG GCG GGC CGG GCC CCC ACG CCG GAG        270
Glu Ala Tyr Gly Gly Tyr Lys Ala Gly Arg Ala Pro Thr Pro Glu
             80                  85                  90

GAC TTT CCC CGG CAA CTC GCC CTC ATC AAG GAG CTG GTG GAC CTC        315
Asp Phe Pro Arg Gln Leu Ala Leu Ile Lys Glu Leu Val Asp Leu
             95                 100                 105

CTG GGG CTG GCG CGC CTC GAG GTC CCG GGC TAC GAG GCG GAC GAC        360
Leu Gly Leu Ala Arg Leu Glu Val Pro Gly Tyr Glu Ala Asp Asp
            110                 115                 120

GTC CTG GCC AGC CTG GCC AAG AAG GCG GAA AAG GAG GGC TAC GAG        405
Val Leu Ala Ser Leu Ala Lys Lys Ala Glu Lys Glu Gly Tyr Glu
            125                 130                 135

GTC CGC ATC CTC ACC GCC GAC AAA GAC CTT TAC CAG CTC CTT TCC        450
Val Arg Ile Leu Thr Ala Asp Lys Asp Leu Tyr Gln Leu Leu Ser
            140                 145                 150

GAC CGC ATC CAC GTC CTC CAC CCC GAG GGG TAC CTC ATC ACC CCG        495
Asp Arg Ile His Val Leu His Pro Glu Gly Tyr Leu Ile Thr Pro
            155                 160                 165

GCC TGG CTT TGG GAA AAG TAC GGC CTG AGG CCC GAC CAG TGG GCC        540
Ala Trp Leu Trp Glu Lys Tyr Gly Leu Arg Pro Asp Gln Trp Ala
            170                 175                 180

GAC TAC CGG GCC CTG ACC GGG GAC GAG TCC GAC AAC CTT CCC GGG        585
Asp Tyr Arg Ala Leu Thr Gly Asp Glu Ser Asp Asn Leu Pro Gly
            185                 190                 195

GTC AAG GGC ATC GGG GAG AAG ACG GCG AGG AAG CTT CTG GAG GAG        630
Val Lys Gly Ile Gly Glu Lys Thr Ala Arg Lys Leu Leu Glu Glu
            200                 205                 210

TGG GGG AGC CTG GAA GCC CTC CTC AAG AAC CTG GAC CGG CTG AAG        675
Trp Gly Ser Leu Glu Ala Leu Leu Lys Asn Leu Asp Arg Leu Lys
            215                 220                 225

CCC GCC ATC CGG GAG AAG ATC CTG GCC CAC ATG GAC GAT CTG AAG        720
Pro Ala Ile Arg Glu Lys Ile Leu Ala His Met Asp Asp Leu Lys
            230                 235                 240

CTC TCC TGG GAC CTG GCC AAG GTG CGC ACC GAC CTG CCC CTG GAG        765
Leu Ser Trp Asp Leu Ala Lys Val Arg Thr Asp Leu Pro Leu Glu
            245                 250                 255

GTG GAC TTC GCC AAA AGG CGG GAG CCC GAC CGG GAG GGG CTT AGG        810
Val Asp Phe Ala Lys Arg Arg Glu Pro Asp Arg Glu Gly Leu Arg
            260                 265                 270

GCC TTT CTG GAG AGG CTT GAG TTT GGC AGC CTC CTC CAC GAG TTC        855
Ala Phe Leu Glu Arg Leu Glu Phe Gly Ser Leu Leu His Glu Phe
            275                 280                 285

GGC CTT CTG GAA AGC CCC AAG GCC CTG GAG GAG GCC CCC TGG CCC        900
Gly Leu Leu Glu Ser Pro Lys Ala Leu Glu Glu Ala Pro Trp Pro
            290                 295                 300

CCG CCG GAA GGG GCC TTC GTG GGC TTT GTG CTT TCC CGC AAG GAG        945
Pro Pro Glu Gly Ala Phe Val Gly Phe Val Leu Ser Arg Lys Glu
            305                 310                 315

CCC ATG TGG GCC GAT CTC CTC GCC CTG GCC GCC GCC AGG GGG GGC        990
Pro Met Trp Ala Asp Leu Leu Ala Leu Ala Ala Ala Arg Gly Gly
```

-continued

|  |  |  |  |  |  |  |  |  |  |  |  |  |
|---|---|---|---|---|---|---|---|---|---|---|---|---|
|  |  |  | 320 |  |  |  | 325 |  |  |  | 330 |  |

| CGG | GTC | CAC | CGG | GCC | CCC | GAG | CCT | TAT | AAA | GCC | CTC | AGG | GAC | CTG | 1035 |
| Arg | Val | His | Arg | Ala | Pro | Glu | Pro | Tyr | Lys | Ala | Leu | Arg | Asp | Leu |  |
|  |  |  | 335 |  |  |  | 340 |  |  |  | 345 |  |

| AAG | GAG | GCG | CGG | GGG | CTT | CTC | GCC | AAA | GAC | CTG | AGC | GTT | CTG | GCC | 1080 |
| Lys | Glu | Ala | Arg | Gly | Leu | Leu | Ala | Lys | Asp | Leu | Ser | Val | Leu | Ala |  |
|  |  |  | 350 |  |  |  | 355 |  |  |  | 360 |  |

| CTG | AGG | GAA | GGC | CTT | GGC | CTC | CCG | CCC | GGC | GAC | GAC | CCC | ATG | CTC | 1125 |
| Leu | Arg | Glu | Gly | Leu | Gly | Leu | Pro | Pro | Gly | Asp | Asp | Pro | Met | Leu |  |
|  |  |  | 365 |  |  |  | 370 |  |  |  | 375 |  |

| CTC | GCC | TAC | CTC | CTG | GAC | CCT | TCC | AAC | ACC | ACC | CCC | GAG | GGG | GTG | 1170 |
| Leu | Ala | Tyr | Leu | Leu | Asp | Pro | Ser | Asn | Thr | Thr | Pro | Glu | Gly | Val |  |
|  |  |  | 380 |  |  |  | 385 |  |  |  | 390 |  |

| GCC | CGG | CGC | TAC | GGC | GGG | GAG | TGG | ACG | GAG | GAG | GCG | GGG | GAG | CGG | 1215 |
| Ala | Arg | Arg | Tyr | Gly | Gly | Glu | Trp | Thr | Glu | Glu | Ala | Gly | Glu | Arg |  |
|  |  |  | 395 |  |  |  | 400 |  |  |  | 405 |  |

| GCC | GCC | CTT | TCC | GAG | AGG | CTC | TTC | GCC | AAC | CTG | TGG | GGG | AGG | CTT | 1260 |
| Ala | Ala | Leu | Ser | Glu | Arg | Leu | Phe | Ala | Asn | Leu | Trp | Gly | Arg | Leu |  |
|  |  |  | 410 |  |  |  | 415 |  |  |  | 420 |  |

| GAG | GGG | GAG | GAG | AGG | CTC | CTT | TGG | CTT | TAC | CGG | GAG | GTG | GAG | AGG | 1305 |
| Glu | Gly | Glu | Glu | Arg | Leu | Leu | Trp | Leu | Tyr | Arg | Glu | Val | Glu | Arg |  |
|  |  |  | 425 |  |  |  | 430 |  |  |  | 435 |  |

| CCC | CTT | TCC | GCT | GTC | CTG | GCC | CAC | ATG | GAG | GCC | ACG | GGG | GTG | CGC | 1350 |
| Pro | Leu | Ser | Ala | Val | Leu | Ala | His | Met | Glu | Ala | Thr | Gly | Val | Arg |  |
|  |  |  | 440 |  |  |  | 445 |  |  |  | 450 |  |

| CTG | GAC | GTG | GCC | TAT | CTC | AGG | GCC | TTG | TCC | CTG | GAG | GTG | GCC | GAG | 1395 |
| Leu | Asp | Val | Ala | Tyr | Leu | Arg | Ala | Leu | Ser | Leu | Glu | Val | Ala | Glu |  |
|  |  |  | 455 |  |  |  | 460 |  |  |  | 465 |  |

| GAG | ATC | GCC | CGC | CTC | GAG | GCC | GAG | GTC | TTC | CGC | CTG | GCC | GGC | CAC | 1440 |
| Glu | Ile | Ala | Arg | Leu | Glu | Ala | Glu | Val | Phe | Arg | Leu | Ala | Gly | His |  |
|  |  |  | 470 |  |  |  | 475 |  |  |  | 480 |  |

| CCC | TTC | AAC | CTC | AAC | TCC | CGG | GAC | CAG | CTG | GAA | AGG | GTC | CTC | TTT | 1485 |
| Pro | Phe | Asn | Leu | Asn | Ser | Arg | Asp | Gln | Leu | Glu | Arg | Val | Leu | Phe |  |
|  |  |  | 485 |  |  |  | 490 |  |  |  | 495 |  |

| GAC | GAG | CTA | GGG | CTT | CCC | GCC | ATC | GGC | AAG | ACG | GAG | AAG | ACC | GGC | 1530 |
| Asp | Glu | Leu | Gly | Leu | Pro | Ala | Ile | Gly | Lys | Thr | Glu | Lys | Thr | Gly |  |
|  |  |  | 500 |  |  |  | 505 |  |  |  | 510 |  |

| AAG | CGC | TCC | ACC | AGC | GCC | GCC | GTC | CTG | GAG | GCC | CTC | CGC | GAG | GCC | 1575 |
| Lys | Arg | Ser | Thr | Ser | Ala | Ala | Val | Leu | Glu | Ala | Leu | Arg | Glu | Ala |  |
|  |  |  | 515 |  |  |  | 520 |  |  |  | 525 |  |

| CAC | CCC | ATC | GTG | GAG | AAG | ATC | CTG | CAG | TAC | CGG | GAG | CTC | ACC | AAG | 1620 |
| His | Pro | Ile | Val | Glu | Lys | Ile | Leu | Gln | Tyr | Arg | Glu | Leu | Thr | Lys |  |
|  |  |  | 530 |  |  |  | 535 |  |  |  | 540 |  |

| CTG | AAG | AGC | ACC | TAC | ATT | GAC | CCC | TTG | CCG | GAC | CTC | ATC | CAC | CCC | 1665 |
| Leu | Lys | Ser | Thr | Tyr | Ile | Asp | Pro | Leu | Pro | Asp | Leu | Ile | His | Pro |  |
|  |  |  | 545 |  |  |  | 550 |  |  |  | 555 |  |

| AGG | ACG | GGC | CGC | CTC | CAC | ACC | CGC | TTC | AAC | CAG | ACG | GCC | ACG | GCC | 1710 |
| Arg | Thr | Gly | Arg | Leu | His | Thr | Arg | Phe | Asn | Gln | Thr | Ala | Thr | Ala |  |
|  |  |  | 560 |  |  |  | 565 |  |  |  | 570 |  |

| ACG | GGC | AGG | CTA | AGT | AGC | TCC | GAT | CCC | AAC | CTC | CAG | AAC | ATC | CCC | 1755 |
| Thr | Gly | Arg | Leu | Ser | Ser | Ser | Asp | Pro | Asn | Leu | Gln | Asn | Ile | Pro |  |
|  |  |  | 575 |  |  |  | 580 |  |  |  | 585 |  |

| GTC | CGC | ACC | CCG | CTT | GGG | CAG | AGG | ATC | CGC | CGG | GCC | TTC | ATC | GCC | 1800 |
| Val | Arg | Thr | Pro | Leu | Gly | Gln | Arg | Ile | Arg | Arg | Ala | Phe | Ile | Ala |  |
|  |  |  | 590 |  |  |  | 595 |  |  |  | 600 |  |

| GAG | GAG | GGG | TGG | CTA | TTG | GTG | GCC | CTG | GAC | TAT | AGC | CAG | ATA | GAG | 1845 |
| Glu | Glu | Gly | Trp | Leu | Leu | Val | Ala | Leu | Asp | Tyr | Ser | Gln | Ile | Glu |  |
|  |  |  | 605 |  |  |  | 610 |  |  |  | 615 |  |

| CTC | AGG | GTG | CTG | GCC | CAC | CTC | TCC | GGC | GAC | GAG | AAC | CTG | ATC | CGG | 1890 |

-continued

```
                    Leu Arg Val Leu Ala His Leu Ser Gly Asp Glu Asn Leu Ile Arg
                                    620                 625                 630

GTC TTC CAG GAG GGG CGG GAC ATC CAC ACG GAG ACC GCC AGC TGG                   1935
Val Phe Gln Glu Gly Arg Asp Ile His Thr Glu Thr Ala Ser Trp
                635                 640                 645

ATG TTC GGC GTC CCC CGG GAG GCC GTG GAC CCC CTG ATG CGC CGG                   1980
Met Phe Gly Val Pro Arg Glu Ala Val Asp Pro Leu Met Arg Arg
                650                 655                 660

GCG GCC AAG ACC ATC AAC TTC GGG GTC CTC TAC GGC ATG TCG GCC                   2025
Ala Ala Lys Thr Ile Asn Phe Gly Val Leu Tyr Gly Met Ser Ala
                665                 670                 675

CAC CGC CTC TCC CAG GAG CTA GCC ATC CCT TAC GAG GAG GCC CAG                   2070
His Arg Leu Ser Gln Glu Leu Ala Ile Pro Tyr Glu Glu Ala Gln
                680                 685                 690

GCC TTC ATT GAG CGC TAC TTT CAG AGC TTC CCC AAG GTG CGG GCC                   2115
Ala Phe Ile Glu Arg Tyr Phe Gln Ser Phe Pro Lys Val Arg Ala
                695                 700                 705

TGG ATT GAG AAG ACC CTG GAG GAG GGC AGG AGG CGG GGG TAC GTG                   2160
Trp Ile Glu Lys Thr Leu Glu Glu Gly Arg Arg Arg Gly Tyr Val
                710                 715                 720

GAG ACC CTC TTC GGC CGC CGC CGC TAC GTG CCA GAC CTA GAG GCC                   2205
Glu Thr Leu Phe Gly Arg Arg Arg Tyr Val Pro Asp Leu Glu Ala
                725                 730                 735

CGG GTG AAG AGC GTG CGG GAG GCG GCC GAG CGC ATG GCC TTC AAC                   2250
Arg Val Lys Ser Val Arg Glu Ala Ala Glu Arg Met Ala Phe Asn
                740                 745                 750

ATG CCC GTC CAG GGC ACC GCC GCC GAC CTC ATG AAG CTG GCT ATG                   2295
Met Pro Val Gln Gly Thr Ala Ala Asp Leu Met Lys Leu Ala Met
                755                 760                 765

GTG AAG CTC TTC CCC AGG CTG GAG GAA ATG GGG GCC AGG ATG CTC                   2340
Val Lys Leu Phe Pro Arg Leu Glu Glu Met Gly Ala Arg Met Leu
                770                 775                 780

CTT CAG GTC CAC GAC GAG CTG GTC CTC GAG GCC CCA AAA GAG AGG                   2385
Leu Gln Val His Asp Glu Leu Val Leu Glu Ala Pro Lys Glu Arg
                785                 790                 795

GCG GAG GCC GTG GCC CGG CTG GCC AAG GAG GTC ATG GAG GGG GTG                   2430
Ala Glu Ala Val Ala Arg Leu Ala Lys Glu Val Met Glu Gly Val
                800                 805                 810

TAT CCC CTG GCC GTG CCC CTG GAG GTG GAG GTG GGG ATA GGG GAG                   2475
Tyr Pro Leu Ala Val Pro Leu Glu Val Glu Val Gly Ile Gly Glu
                815                 820                 825

GAC TGG CTC TCC GCC AAG GAG TGA                                               2499
Asp Trp Leu Ser Ala Lys Glu
                830

(2) INFORMATION FOR SEQ ID NO:2:

(i) SEQUENCE CHARACTERISTICS:
          (A) LENGTH:  33
          (B) TYPE:  nucleic acid
          (C) STRANDEDNESS:  double
          (D) TOPOLOGY:  linear (xi) SEQUENCE DESCRIPTION:  SEQ ID NO:2:

ATG CGT GGT ATG CTG CCT CTG TTT GAG CCG AAG                                     33
Met Arg Gly Met Leu Pro Leu Phe Glu Pro Lys
1               5                   10
```

(2) INFORMATION FOR SEQ ID NO:3:

(i) SEQUENCE CHARACTERISTICS:
        (A) LENGTH: 33

(B) TYPE: nucleic acid (C) STRANDEDNESS: double (D) TOPOLOGY: linear (xi) SEQUENCE DESCRIPTION: SEQ ID NO:3:

```
ATG CGT GGG ATG CTG CCC CTC TTT GAG CCC AAG                    33
Met Arg Gly Met Leu Pro Leu Phe Glu Pro Lys
1               5                   10
```

(2) INFORMATION FOR SEQ ID NO:4:

(i) SEQUENCE CHARACTERISTICS:
        (A) LENGTH: 57

(B) TYPE: nucleic acid (C) STRANDEDNESS: double (D) TOPOLOGY: linear (xi) SEQUENCE DESCRIPTION: SEQ ID NO:4:

```
ATG GAC TAC AAG GAC GAC GAT GAC AAG CGT GGT ATG                36
Met Asp Tyr Lys Asp Asp Asp Asp Lys Arg Gly Met
1               5                   10

CTG CCC CTC TTT GAG CCC AAG                                    57
Leu Pro Leu Phe Glu Pro Lys
        15
```

(2) INFORMATION FOR SEQ ID NO:5:

(i) SEQUENCE CHARACTERISTICS:
        (A) LENGTH: 57

(B) TYPE: nucleic acid (C) STRANDEDNESS: double (D) TOPOLOGY: linear (xi) SEQUENCE DESCRIPTION: SEQ ID NO:5:

```
ATG GAC TAC AAG GAC GAC GAT GAC AAG                            27
Met Asp Tyr Lys Asp Asp Asp Asp Lys
1               5

AGG GGG ATG CTG CCC CTC TTT GAG CCC AAG                        57
Arg Gly Met Leu Pro Leu Phe Glu Pro Lys
10                  15
```

(2) INFORMATION FOR SEQ ID NO:6:

(i) SEQUENCE CHARACTERISTICS:
        (A) LENGTH: 20

(B) TYPE: nucleic acid (C) STRANDEDNESS: single (D) TOPOLOGY: linear (xi) SEQUENCE DESCRIPTION: SEQ ID NO:6:

```
GAATTC ATG AGG GGG ATG CT                                                    20

(2) INFORMATION FOR SEQ ID NO:7:

(i) SEQUENCE CHARACTERISTICS:
        (A) LENGTH:  23

(B) TYPE:  nucleic acid (C) STRANDEDNESS:  single (D) TOPOLOGY:  linear (xi) SEQUENCE DESCRIPTION:  SEQ ID NO:7:

GGTGGAAT TCA CTC CTT GGC GGA                                                 23

(2) INFORMATION FOR SEQ ID NO:8:

(i) SEQUENCE CHARACTERISTICS:
        (A) LENGTH:  24

(B) TYPE:  nucleic acid (C) STRANDEDNESS:  double (D) TOPOLOGY:  linear (xi) SEQUENCE DESCRIPTION:  SEQ ID NO:8:

GAC TAC AAG GAC GAC GAT GAC AAG                                              24
Asp Tyr Lys Asp Asp Asp Asp Lys
1               5

(2) INFORMATION FOR SEQ ID NO:9:

(i) SEQUENCE CHARACTERISTICS:
        (A) LENGTH:  9 amino acids (B) TYPE:  amino acid (C) STRANDEDNESS:  single (D) TOPOLOGY:  linear (ii) MOLECULE TYPE:  protein (xi) SEQUENCE DESCRIPTION:  SEQ ID NO:9:

Met Asp Tyr Lys Asp Asp Asp Asp Lys
1               5

(2) INFORMATION FOR SEQ ID NO:10:

(i) SEQUENCE CHARACTERISTICS:
        (A) LENGTH:  18

(B) TYPE:  nucleic acid (C) STRANDEDNESS:  single (D) TOPOLOGY:  linear (xi) SEQUENCE DESCRIPTION:  SEQ ID NO:10:

GTGGTCTTTG ACGCCAAG                                                          18

(2) INFORMATION FOR SEQ ID NO:11:

(i) SEQUENCE CHARACTERISTICS:
```

(A) LENGTH: 59

(B) TYPE: nucleic acid (C) STRANDEDNESS: single (D) TOPOLOGY: linear (xi) SEQUENCE DESCRIPTION: SEQ ID NO:11:

AGGGGCAGCA TACCACGCTT GTCATCGTCG TCCTTGTAGT CCATAATTCT GTTTCCTGT        59

(2) INFORMATION FOR SEQ ID NO:12:

(i) SEQUENCE CHARACTERISTICS:
        (A) LENGTH: 60

(B) TYPE: nucleic acid (C) STRANDEDNESS: single (D) TOPOLOGY: linear (xi) SEQUENCE DESCRIPTION: SEQ ID NO:12:

AGGGGCAGCA TCCCCCTCTT GTCATCGTCG TCCTTGTAGT CCATGAATTC TGTTTCCTGT        60

(2) INFORMATION FOR SEQ ID NO:13:

(i) SEQUENCE CHARACTERISTICS:
        (A) LENGTH: 48

(B) TYPE: nucleic acid (C) STRANDEDNESS: single (D) TOPOLOGY: linear (xi) SEQUENCE DESCRIPTION: SEQ ID NO:13:

GCCCTTCGGC TCAAACAGTG GCAGCATACC ACGCATAATT CTGTTTCC                    48

(2) INFORMATION FOR SEQ ID NO:14:

(i) SEQUENCE CHARACTERISTICS:
        (A) LENGTH: 53

(B) TYPE: nucleic acid (C) STRANDEDNESS: single (D) TOPOLOGY: linear (xi) SEQUENCE DESCRIPTION: SEQ ID NO:14:

CGGCCCTTGG GCTCAAAGAG GGGCAGCATC CCACGCATGA ATTCCTGTTTCCT              53

INCREASED PRODUCTION OF *THERMUS AQUATICUS* DNA POLYMERASE IN *E. COLI*

II. FIELD OF THE INVENTION

This invention relates to the field of genetic engineering. More particularly, this invention relates to the alteration of a native gene to provide a mutant form having improved expression in *E. coli*.

III. BACKGROUND OF THE INVENTION

One of the major achievements in recombinant technology is the high-level expression (overproduction) of foreign proteins in procaryotic cells such as *Escherichia coli* (*E. coli*). In recent years, this technology has improved the availability of medically and scientifically important proteins, several of which are already available for clinical therapy and scientific research. Overproduction of protein in procaryotic cells is demonstrated by directly measuring the activity of the enzyme with a suitable substrate or by measuring the physical amount of specific protein produced. High levels of protein production can be achieved by improving expression of the gene encoding the protein. An important aspect of gene expression is efficiency in translating the nucleotide sequence encoding the protein. There is much interest in improving the production of bacterial enzymes that are useful reagents in nucleic acid biochemistry itself, for example, DNA ligase, DNA polymerase, etc.

Unfortunately, this technology does not always provide high protein yields. One cause of low protein yield, is inefficient translation of the nucleotide sequences encoding the foreign protein. Amplification of protein yields depends, inter alia, upon ensuring efficient translation.

Through extensive studies in several laboratories, it is now recognized that the nucleotide sequence at the N-terminus-encoding region of a gene is one of the factors strongly influencing translation efficiency. It is also recognized that alteration of the codons at the beginning of the gene can overcome poor translation. One strategy is to redesign the first portion of the coding sequence without altering the amino acid sequence of the encoded protein, by using the known degeneracy of the genetic code to alter codon selection.

However, the studies do not predict, teach, or give guidance as to which bases are important or which sequences should be altered for a particular protein. Hence, the researcher must adopt an essentially empirical approach when he attempts to optimize protein production by employing these recombinant techniques.

An empirical approach is laborious. Generally, a variety of synthetic oligonucleotides including all the potential codons for the correct amino acid sequence is substituted at the N-terminus encoding region. A variety of methods can then be employed to select or screen for one oligonucleotide which gives high expression levels. Another approach is to obtain a series of derivatives by random mutagenesis of the original sequence. Extensive screening methods will hopefully yield a clone with high expression levels. This candidate is then analyzed to determine the "optimal" sequence and that sequence is used to replace the corresponding fragments in the original gene. This shot-gun approach is laborious.

These tedious strategies are employed to amplify the synthesis of a desired protein which is produced by the unaltered (native) gene only in small quantities. The thermostable DNA polymerase from *Thermus aquaticus* (Taq Pol) is such a product.

Taq Pol catalyzes the combination of nucleotide triphosphates to form a nucleic acid strand complementary to a nucleic acid template strand. The application of thermostable Taq Pol to the amplification of nucleic acid by polymerase chain reaction (PCR) was the key step in the development of PCR to its now dominant position in molecular biology. The gene encoding Taq Pol has been cloned, sequenced, and expressed in *E. coli*, yielding only modest amounts of Taq Pol.

The problem is that although Taq Pol is commercially available from several sources, it is expensive, partly because of the modest amounts recovered by using the methods currently available. Increased production of Taq Pol is clearly desirable to meet increasing demand and to make production more economical.

IV. BRIEF DESCRIPTION OF THE DRAWING

FIG. 1, the sole illustration, shows the relevant genetic components of a vector, pSCW562, used to transform an *E. coli* host.

V. SUMMARY OF THE INVENTION

The present invention provides a gene for Taq polymerase wherein the sequence of the first thirty nucleotide bases in the native gene which code for the first ten amino acids in the mature native protein, has been changed A) by substituting therefor a modified nucleotide sequence selected from the group consisting of:
SEQ ID NO: 2: ATG CGT GGT ATG CTG CCT CTG TTT GAG CCG AAG, 33
SEQ ID NO: 3: ATG CGT GGG ATG CTG CCC CTC TTT GAG CCC AAG, and 33
SEQ ID NO: 4: ATG GAC TAC AAG GAC GAC GAT GAC AAG CGT GGT ATG 36 CTG CCC CTC TTT GAG CCC AAG, 57 or

B) by inserting between the codon (ATG) for the first amino acid of the mature native protein and the codon, (AGG) for the second amino acid of the mature native protein, the sequence:
SEQ ID NO: 8: GAC TAC AAG GAC GAC GAT GAC AAG. 24

The invention also provides a method of increasing the production of Taq Pol by using the above altered genes.

The invention describes enhanced polymerase activity levels as high as 200-fold. The recombinant polymerase of this invention is functionally indistinguishable from native Taq Pol.

VI. Details of the Invention

1. Introduction

The object of the present invention is to increase the production of Taq polymerase in *E. coli* by changing selected nucleotide sequences in the 5' region of the gene which encode the N-terminus of the polymerase.

The invention provides four nucleotide sequences which differ from the native *Thermus aquaticus* polymerase (Taq Pol) gene in one to several nucleotides. When introduced into the native gene and transfected into *E. coli*, these DNA sequences provide improved expression of the gene, evidenced by increased activity of the enzyme. The amount of increase varies widely depending on the nucleotide changes made and also on other factors such as induction with IPTG, incubation period of *E. coli*, etc.

The genes provided by the present invention are the same as the native Taq Pol gene except for changes in the native sequence made in accordance with the present invention. Where these changes are made, they are specifically described and shown in the examples and in the Sequence Listing. Changes are only in the region encoding the N-terminus of the protein. More specifically, changes are made only in the region upstream of the eleventh codon (AAG) coding for the eleventh amino acid (lysine) in the mature native protein. The eleventh codon is not changed, but it is shown in the sequence listing as the bracket or the point above which changes are made in the practise of the invention. Except for these identified changes, the remaining sequence of the Taq Pol gene remains unchanged.

The term "Taq Pol gene" as used herein refers to the nucleotide sequence coding for the thermostable DNA polymerase of *Thermus aquaticus* and includes mutant forms, spontaneous or induced, of the native gene as long as the mutations do not confer substantial changes in the essential activity of the native polymerase The term "Taq Pol" as used herein refers to the polymerase encoded by the Taq Pol gene.

The term "native" as used herein refers to the unaltered nucleotide sequence of the Taq Pol gene or the unaltered amino acid sequence of the Taq polymerase as that gene or enzyme occurs naturally in *T. aquaticus*. See SEQ ID NO:1.

In general terms, the invention comprises the following steps:

A) providing a vector with a Taq Pol gene of the invention,

B) transfecting compatible *E. coli* host cells with the vector of A) thereby obtaining transformed *E. coli* host cells; and C) culturing the transformed cells of B) under conditions for growth thereby producing Taq polymerase synthesized by the transformed host cells.

The following bacterial strains, plasmids, phage and reagents were used in the invention.

2. Bacterial Strains

*Thermus aquaticus* YT-I, ATCC No. 25104, was used for native DNA isolation. The host *E. coli* strain for all cloning and plasmid manipulation, DH5α [F⁻Ø80dlacZΔM15 Δ(lacZYA-argF)U169 recAl endAl hsdR17(r⁻$_K$, m⁺$_K$) supE44 thil gyrA relAl] was obtained from BRL.

Strain JM103 [thi⁻, strA, supE, endA, sbcB, hsdR⁻, D(lac-pro), F' traD36, proAB, lacI$^q$, lacZDM15] (Yanisch-Perron et al., Improved M13 Phage Cloning Vectors and Host Strains: Nucleotide Sequences of M13mp18 and pUC19 Vectors, Gene 33:103–119 (1985)) was also utilized for protein expression experiments.

The host strain for preparation of single-stranded DNA for use in mutagenesis was CJ236 (pCJ105, dut ung thi relA) (Kunkel et al., Rapid and Efficient Site-specific Mutagenesis without Phenotypic Selection, Methods Enzymol 154:367–382, (1987)).

The fl phage R408 (Russel et al., An Improved Filamentous Helper Phage for Generating Single-stranded DNA, Gene 45:333–338 (1986)) was used as the helper to generate single-stranded plasmid DNA for mutagenesis. The plasmid used for all cloning and expression work was pSCW562 or its derivative pTaq1. A diagram of pSCW562 is shown in FIG. 1. When the native Taq Pol gene is inserted into pSCW562, the resulting plasmid is designated pTaq1. When the native Taq Pol gene is altered by mutagenesis, the mutant plasmid is designated pTaq3, pTaq4, pTaq5, or pTaq6 depending on the nucleotide sequence with which it is mutagenized.

3. Reagents

Chemicals were purchased from Sigma, International Biotechnologies, Inc. or Eastman Kodak. LB medium was obtained from Gibco. Enzymes were purchased from New England Biolabs, IBI, BRL, Boehringer-Mannheim, or U.S. Biochemicals and were used as recommended by the supplier. Sequenase™ kits for DNA sequencing were obtained from U.S. Biochemicals. Radioisotopes were purchased from Amersham. Taq polymerase was purchased from Cetus.

4. Method of Increasing the Production of Tag Pol

Step A—Providing a Vector with the Tag Pol Gene of the Invention

One method of providing a vector with the Taq Pol gene of the invention is to:

provide the native DNA from *Thermus aquaticus;* amplify the native Taq Pol DNA and incorporate restriction sites at both ends of the DNA fragments, ligate the DNA fragments of ii) into a suitable vector, use site-directed mutagenesis to change the nucleotide sequence of of the native DNA, and screen for vectors carrying the changed nucleotide sequence of the invention.

i. Providing the Native Gene from *T. aquaticus*

All DNA manipulations were done using standard protocols (Maniatis et al, Molecular Cloning: A Laboratory Manual, Cold Spring Harbor Laboratory, Cold Spring Harbor, N.Y., 1982 and Ausebel et al, Current Protocols in Molecular Biology, John Wiley and Sons, New York, N.Y., 1987). Total DNA from *T. aquaticus* (strain YT-1, [ATCC No. 25104]) was isolated from a 40 mL culture of the organism grown overnight at 70° C. in ATCC medium #461. The cells were pelleted by centrifugation, washed once with 10 mM tris HCl, pH 8.0, 1 mM ethylendiaminetetraacetic acid (EDTA), 10 mM Tris HCl (pH 8.0) (TE), and resuspended in 5 mL of TE. Lysozyme was added to a concentration of 1 mg/mL and the solution was incubated at 37° C. for 30 minutes. EDTA, sodium dodecyl sulfate (SDS) and proteinase K were added to concentrations of 50 mM, 0.5% and 100 μg/mL, respectively, and the solution was incubated for 4 hours at 50° C. The sample was extracted three times with phenol-chloroform and once with chloroform and the DNA was precipitated by addition of sodium acetate to 0.3 M and two volumes of ethanol. The DNA was collected by spooling on a glass rod, washed in 70% ethanol, and dissolved in (TE).

ii. Amplifying the Native Tag Pol Gene and Incorporating Restriction Sites

The fastest approach to producing large amounts of Taq Pol gene is to utilize the published nucleic acid sequence of the gene (Lawyer et al, Isolation, Characterization and Expression in *Escherichia coli* of the DNA Polymerase from *Thermus aquaticus*, Journal of Biological Chemistry, 264:6427–6437, 1989) to design oligonucleotide primers that can be used in PCR to amplify genomic DNA. See SEQ ID NO: 1: for entire gene sequence.

PCR is an amplification technique well known in the art (Saiki et al., Primer-directed Enzymatic Amplification of DNA with a Thermostable DNA Polymerase, Science 239:487–491 (1988)), which involves a chain reaction producing large amounts of a specific known nucleic acid sequence. PCR requires that the nucleic acid sequence to be amplified must be known in sufficient detail so that oligonucleotide primers can be prepared which are sufficiently complementary to the desired nucleic acid sequences, as to hybridize with them and synthesize extension products.

Primers are oligonucleotides, natural or synthetic, which are capable of acting as points of initiation for DNA synthesis when placed under conditions in which synthesis of a primer extension product which is complementary to a nucleic acid strand is induced, i.e., in the presence of four different nucleotide triphosphates and thermostable enzymes in an appropriate buffer and at a suitable temperature.

PCR amplification was carried out on the Taq Pol DNA of i) essentially as described by Saiki et al, in an Ericomp thermocycler. Primers were designed based upon the published sequence of the Taq Pol gene (Lawyer et al.). Amplification mixtures contained approximately 100 ng of *T. aquaticus* DNA, 1 $\mu$M of each of the two primers, 200 $\mu$M each of dATP, dGTP, dCTP and dTTP, and 2 units of Taq Pol in a volume of 0.05 mL. The mixtures were heated to 97° C. for 10 seconds, annealed at 40° C. for thirty seconds, and extended at 72° C. for 5 minutes for 5 cycles. For the subsequent 20 cycles, the annealing temperature was raised to 55° C. and the extension time reduced to 3 minutes. Finally, the mixtures were incubated at 72° C. for 15 minutes to maximize the amount of fully double-stranded product. The entire PCR reaction mixture was fractionated on a 1.0% agarose gel and the 2.5 kb Taq polymerase gene was cut out and extracted. DNA fragments were isolated from agarose gels using a "freeze-squeeze technique". Agarose slices were minced, frozen on dry ice, and rapidly thawed at 37° C. for five minutes. The slurry was filtered by centrifugation through a Millipore 0.45 $\mu$m Durapore membrane. The filtrate was extracted once with water saturated phenol, once with phenol-chloroform (1:1), and once with chloroform. The DNA was recovered by ethanol precipitation.

Incorporating Restriction Sites: To allow excision and recovery of the Taq Pol gene during PCR and also to afford convenient cloning of the Taq Pol gene into an expression vector, two restriction sites were introduced at the 5' ends of both strands of the gene. More specifically, one restriction site was introduced adjacent to and upstream from the start (ATG) codon and the other restriction site was introduced adjacent to and downstream from the stop (TGA) codon (SEQ ID NOS: 6 & 7). The nucleotides forming the restriction sites were included on the synthetic primer used in the PCR. In the examples disclosed herein, the nucleotide sequence GAATTC, which forms EcoRl restriction site was included on the primers.

Other restriction sites may be used in the practice of this invention provided that 1) the expression vector has a corresponding site where the Taq DNA is to be ligated, 2) the restriction site does not occur within the Taq Pol gene.

As shown in FIG. 1, EcoRl is one of several restriction sites in pSCW562. Other exemplary restriction sites are XbaI and SphI. Of course, expression vectors having other restriction sites would provide still more potential restriction sites which would be useful in the practice of this invention.

When digested with the appropriate enzyme, these restriction sites form sticky ends which can be conveniently ligated to correspondingly digested restriction sites on the expression vector. The restriction sites do not affect the amino acid sequence of Taq Pol.

Alternative Method: In lieu of the PCR technique described above, the native Taq Pol gene may alternatively be provided by conventionally cloning the gene. In that event, the restriction sites may be introduced by site directed mutagenesis. The end results of either procedure are indistinguishable.

iii. Ligating DNA Fragments into a Vector

The DNA from step ii) is then ligated to a suitable expression vector. The vector chosen for cloning was pSCW562, which contains an EcoRl site 11 base pairs downstream of the ribosome binding site and the strong tac (trp-lac hybrid) promoter (FIG. 1). The Taq Pol gene does not contain any EcoRl sites, so the PCR primers were designed with EcoRl sites near their 5' ends (step ii)) to allow direct cloning into the EcoRl site of pSCW562.

In addition to the EcoRl site, vector pSCW562 contains 1) a phage origin of replication ($F_1$), 2) a plasmid origin of replication (ORI), 3) an antibiotic resistance marker (AMP), and 4) a transcription termination sequence downstream of the restriction sites. This plasmid was constructed using techniques well known in the art of recombinant DNA as taught in Maniatis et al., Molecular Cloning: A Laboratory Manual, Cold Spring Harbor, N.Y. (1982). However, this particular plasmid is not critical to the invention. Any vector containing an appropriate promoter and restriction sites will be useful in this method.

The EcoRl-digested PCR product from Step ii) was fractionated in a 1% agarose gel and eluted. The vector, pSCW562, was digested overnight with EcoRl (10 units/$\mu$g) and treated with calf intestinal alkaline phosphatase (1 unit/$\mu$g), extracted with phenol/chloroform, ethanol precipitated, and resuspended in TE. Approximately 200 ng of the prepared vector was mixed with about 500 ng of purified PCR product and ligated for 18 hours in 50 mM TrisHCl, pH 7.8, 10 mM $MgCl_2$, 20 mM dithiothreitol, 1 mM ATP, with 0.5 Weiss units of T4 DNA ligase in a volume of 20 $\mu$L.

iv. Using Site-Directed Mutagenesis to Change the Nucleotide Sequence of the Native Tag Pol Gene Site-directed mutagenesis is a method of altering the nucleotide sequence of a DNA fragment by specifically substituting, inserting or deleting selected nucleotides within the sequence to be altered. The method involves priming in vitro DNA synthesis with chemically synthesized nucleotides that carry a nucleotide mismatch with the template sequence. The synthetic oligonucleotide primes DNA synthesis and is itself incorporated into the resulting heteroduplex molecule After transformation of host cells, this heteroduplex gives rise to homoduplexes whose sequences carry the mutagenic nucleotides. Mutant clones are selected by screening procedures well known in the art such as nucleic acid hybridization with labelled probes and DNA sequencing.

Using site-directed mutagenesis, we constructed mutant genes for Taq polymerase wherein the sequence of the first thirty nucleotide bases in the native gene which code for the first ten amino acids in the mature native protein, was changed A) by substituting therefor a modified nucleotide sequence selected from the group consisting of:
Example 1—SEQ ID NO: 2: ATG CGT GGT ATG CTG CCT CTG TTT GAG CCG AAG, 33
Example 2—SEQ ID NO: 3: ATG CGT GGG ATG CTG CCC CTC TTT GAG CCC AAG, and 33
Example 3—SEQ ID NO: 4: ATG GAC TAC AAG GAC GAC GAT GAC AAG CGT GGT ATG 36 CTG CCC CTC TTT GAG CCC AAG, 57 or,
Example 4,
B) by inserting between the start: codon (ATG) for the first amino acid of the mature native protein and the codon, (AGG) for the second amino acid of the mature native protein, the sequence:
SEQ ID NO: 8: GAC TAC AAG GAC GAC GAT GAC AAG. 24

SEQ ID NO: 5 presented in the Sequence Listing shows the first 11 codons of the Taq Pol gene with SEQ ID NO: 8 inserted between codons 1 and 2. SEQ ID NO: 9 in the Sequence Listing shows the amino acid sequence corresponding to the first 9 codons of SEQ ID NO: 5.

In the examples above, bases that are changed are highlighted in bold type. The effect that these changes have on polymerase activity is shown in Table I. The above examples are offered by way of illustration only and are by no means intended to limit the scope of the claimed invention.

In these examples all gene modifications were carried out by site-directed mutagenesis. However, alternative methods are known in the art which would give the same results. For example, the changes to the Taq Pol gene described above could have been incorporated directly into the gene during amplification (PCR) by appropriately designing the upstream oligonucleotide primer to include the nucleotide sequences of the invention.

Another alternative would be to incorporate unique restriction sites bracketing the first ten codons of the gene. This would allow removal of the sequences encoding the amino terminus by restriction endonuclease cleavage and replacement using a double stranded synthetic fragment. Either of these methods could be used to accomplish the nucleotide changes set forth above.

Mutagenesis was carried out essentially as described by Kunkel et al, Rapid and Efficient Site-specific Mutagenesis without Phenotypic Selection, Methods Enzymol, 154:367–382, (1987), using a kit obtained from Bio Rad. Single-stranded plasmid DNA was prepared by infecting early exponential phase cultures of CJ236 (carrying pTaqI) with R408 at a multiplicity of infection of approximately 10–20. After overnight growth at 37° C., the cells were removed by centrifugation and the phage precipitated by addition of polyethylene glycol to 5% and NaCl to 0.5 M. The phage were pelleted by centrifugation and the DNA isolated by phenol-chloroform extraction and ethanol precipitation. The mutagenic oligonucleotides SEQ ID NO; 11, SEQ ID NO: 12, SEQ ID NO: 13 and SEQ ID NO: 14 shown in the Sequence Listing were phosphorylated with T4 polynucleotide kinase and 9 pmol of each was annealed to approximately 3 pmol of single-stranded plasmid DNA. The annealed mixture was extended with T4 DNA polymerase, ligated, and transformed into DH5α or JM103. Plasmid DNA was isolated from the transformants by rapid boiling (Holmes and Quigley, A Rapid Boiling Method for the Preparation of Bacterial Plasmids, Anal. Biochem. 114:193–199, 1981) and digested with EcoRl to identify clones that had undergone mutagenesis.

V. Screening for Vectors with the Tag Pol Gene

To verify that the clones of iv) were carrying the desired Taq Pol gene, clones were lifted on to nitrocellulose filters and identified as Taq Pol transformants by colony hybridization.

Colony Hybridization: This technique identifies a specific nucleic acid sequence by creating conditions for single strands of the specific nucleic acid sequence to base pair (hybridize) with a complementary radioactive single stranded nucleic acid fragments (probes). Double-stranded regions form where the two types of DNA have complementary nucleotide sequences and are detected by their radioactivity.

Colonies containing the Taq Pol fragment were identified by hybridization with an internal oligonucleotide:

SEQ ID NO: 10: GTGGTCTTTG ACGCCAAG, labelled with $^{32}$P at the 5' end with T4 polynucleotide kinase. Colony hybridizations were performed as described in Maniatis et al., supra in 5× SSPE [1×SSPE in 10 mM sodium phosphate, pH 7.0, 0.18 M NaCl, 1 mM EDTA], 0.1% sodium lauroyl sarcosine, 0.02% SDS, 0.5% blocking agent (Boehringer-Mannheim) containing approximately 5 ng per mL $^{32}$P labelled oligonucleotide. Hybridization was conducted at 42° C. for 4–18 hours. The filters were washed in 2× SSPE, 0.1% SDS at room temperature three times, followed by a stringent wash at 42° C. in the same solution. Positive colonies were identified by autoradiography.

Sequence Analysis: To ascertain whether or not the Taq Pol DNA was incorporated in the correct orientation, DNA sequence analysis was performed on alkaline denatured supercoiled DNA as described by Zhang et al, Double Stranded DNA sequencing as a Choice for DNA Sequencing, Nucleic Acids Research 16:1220 (1988), using a Sequenase™ kit from U.S. Biochemicals and a ($^{35}$S)dATP. Typically, 1.0 µL of supercoiled, CsCl-banded DNA was denatured in 20 µL of 0.2 M NaOH, 0.2 mM EDTA for 5 minutes. The solution was neutralized with 2 µL of 2 M ammonium acetate (pH 4.6) and precipitated with 60 µL of ethanol. The mixture was centrifuged for 10 minutes, washed once with 80% ethanol, dried for 10 minutes and resuspended in 7 mL of H$_2$O. After addition of 5 ng of primer and 2 µL of 5X buffer, the samples were heated to 65° C. and allowed to cool to <37° C. over 30–45 minutes. The sequencing reactions were then performed as directed by the supplier. The reactions were then performed as directed by the supplier. The reactions were electrophoresed on 6% sequencing gels, occasionally utilizing a sodium acetate salt gradient to improve resolution near the bottom of the gel (Sheen et al, Electrolyte Gradient Gels for DNA Sequencing, Bio Techniques 6:942–944, 1989). Alternatively, plasmid DNA prepared by the rapid boiling or alkaline miniprep procedures was used for sequencing after extraction with phenol-chloroform and ethanol precipitation, although with some reduced reliability.

Step B—Transfecting Host Cells with the Vector of A)

The vector of step A) is used to transfect a suitable host and the transformed host is cultured under favorable conditions for growth. Procaryotic hosts are in general the most efficient and convenient in genetic engineering techniques and are therefore preferred for the expression of Taq polymerase. Procaryotes most frequently are represented by various strains of E. coli such as DH5α and JM103, the strains used in the examples below. However, other microbial strains may also be used, as long as the strain selected as host is compatible with the plasmid vector with which it is transformed. Compatibility of host and plasmid/vector means that the host faithfully replicates the plasmid/vector DNA and allows proper functioning of the above controlling elements. In our system, DH5α and JM103 are compatible with pSCW562.

Five µL of the ligation mixture of Step B were mixed with 0.1 µL of DH5α or JM103 cells made competent by CaCl$_2$ treatment as described by Cohen et al, Proc. National Academy of science, USA, 69:2110 (1972). After incubation on ice for 15–30 minutes, the mixture was incubated at 42° C. for 90 seconds. After the heat shock, one mL of LB medium was added and the cells were incubated for one hour at 37° C.

Selection of Transformants: After the one-hour incubation, aliquots of the incubated mixture were spread on LB agar plates containing 50 µg/mL ampicillin and incubated at 37° C. for 18 hours. Only transformed E. coli carrying the AMP (marker) gene can grow on this medium. To select transformants that were also carrying the Taq Pol gene in correct orientation, colony hybridization and sequence analysis were done using techniques already described above.

Step C—Culturing the Transformed Hosts

E. coli transformants verified as containing the Taq Pol gene in the correct orientation, were cultured in 40 mL of LB broth at 37° C. to mid-log phase and where appropriate, were induced with 1 mM isopropyl-β-D-thiogalactoside (IPTG). The cells were allowed to grow for either an additional two hours or overnight, and were harvested by centrifugation. The cells were resuspended in 0.25 mL of 50 mM trisHCl, pH 7.5, 1 mM EDTA, 0.5 µg/mL leupeptin, 2.4 mM phenylmethylsulphonyl fluoride and sonicated. The lysate was diluted with 0.25 mL of 10 mM TrisHCl, pH 8.0, 50 mM KCl, 0.5% Tween 20, 0.5% NP-40 and heated to 74° C. for 20 minutes. After cooling on ice for 15 minutes, the debris was removed by centrifugation for 10 minutes at 4° C. Aliquots of the supernatant fraction were assayed for DNA polymerase activity using activated salmon sperm DNA as the substrate.

DNA Polymerase Assay: This assay is based on the ability of DNA polymerases to fill in single strand gaps made in double stranded DNA. It uses the single strand gaps as templates and the free 3' hydroxyl group at the border of the single strand gap as the primer at which it begins synthesis. Specifically, 5 µL of enzyme preparation was incubated for 10 minutes at 74° C. in a total of 50 pL with the following: 25 mM Tris(hydroxymethyl)methyl-3-amino-propane sulfonic acid (TAPS) (pH 9.8 at 22° C.), 50 mM KCl, 1 mM 2-mercaptoethanol, 2 mM $MgCl_2$ 0.30 mg/mL activated salmon testes DNA, 0.2 mM of each dCTP, dGTP, dTTP, and 0.1 mM (200 nCi/nmol) [8-$^3$H]dATP. The reaction was stopped by the addition of 100 µL of 0.15 M sodium pyrophosphate, 0.105 M sodium EDTA, pH 8.0, followed by the addition of ice cold 10% trichloroacetic acid (TCA). It was then kept on ice for 15–30 minutes prior to being vacuum filtered on a prewet 25 mm Whatman glass fiber filters (GFC) filter disk. The precipitated reaction product was washed free of unincorporated $^3$H on the filter with a total of 12 mL of ice cold 10% TCA followed by a total of 12 mL of ice cold 95% ethanol. Filters were vacuum dried, then air dried, and then counted directly in a scintillation fluid. Enzyme preparations that required diluting were diluted with a solution of 10 mM Tris, 50 mM KCl, 10 mM $MgCl_2$, 1.0 mg/mL gelatin, 0.5% nonidet P40, 0.5% Tween 20, 1 mM 2-mercaptoethanol, pH 8.0. One unit of activity is the amount of enzyme required to incorporate 10 nmol of total nucleotide in 30 min at 74° C.; adenine constitutes approximately 29.7% of the total bases in salmon sperm DNA.

Salmon testes DNA (Sigma type III; product #D1626) was dissolved to 1.3 mg/mL in TM buffer (10 mM Tris, 5 mM $MgCl_2$, pH 7.2) and stirred slowly for 24 hours at 4° C. It was then diluted 2.5 fold with TM buffer and made 0.3 M in NaCl prior to extracting at room temperature with an equal volume of phenol/chloroform (1:1::vol:vol; phenol saturated with TM buffer). The mixture was centrifuged at 2700×g for 5 minutes at room temperature to aid separation of the phases, the aqueous phase was collected and extracted with an equal volume of chloroform. The mixture was centrifuged as above and the aqueous phase again collected. The activated DNA in the aqueous phase was precipitated with two volumes of 95% ethanol at −20° C.; the precipitated mixture was kept at −20° C. for 12–18 hours. The precipitated DNA was collected by centrifuging at 13,700×g for 30 minutes at 2° C. The pellet was dried with a stream of nitrogen gas and then redissolved 3–6 mg/mL with TE (10 mM Tris, 1 mM EDTA, pH 7.5) with slow rocking for 12–18 hours at room temperature. The solution was dialyzed against TE and then adjusted to the proper concentration by checking the absorbance at 260 nm. Aliquots (0.5–1.0 mL) were stored at −20° C.; for use, one vial was thawed and then kept at 4° C. rather than refreezing.

5. Results of Polymerase Assay

The results of the Taq Pol assay are shown in Table I. Vector pTaq1 carries SEQ ID NO:1 which is the native Taq Pol sequence, while the other four plasmids carry sequences which are altered in accordance with the invention as described above.

Table I shows, unexpectedly, that pTaq3 (SEQ ID NO: 2) expressed Taq Pol activity up to 200 times that of pTaq1; pTaq4 (SEQ ID NO: 3) had about 10 times the activity of pTaq1; pTaq5 (SEQ ID NO: 4) was about 10–50 times greater than pTaq1, depending on the experiment, and pTaq6 (SEQ NO: 8) was at least 10 times as great as pTaq1 (SEQ ID NO: 1). These results are unexpected.

The short nucleotide sequences in the Sequence Listing represent sequence changes in the first 30 nucleotides of the native gene. It is to be understood that these sequences represent only a small fraction of the complete Taq Pol gene which in its entirety contains over 2,000 nucleotides.

TABLE I

| | Taq Pol Activity (Units/mg of protein) | | | | | | |
|---|---|---|---|---|---|---|---|
| Host Strain: | DH5α | DH5α | JM103 | JM103 | JM103 | JM103 | JM103 |
| Time of Harvest: | O/N | O/N | 2 Hr. | 2 Hr. | O/N | 2 Hr. | 2 Hr. |
| Induction | − | + | + | + | + | − | + |
| Plasmid | | | | | | | |
| SEQ ID NO: 1 | | | | | | | |
| pTaq1 SEQ ID NO: 2 | 40 | 90 | 100 | 270 | 1030 | 60 | 180 |
| pTaq3 SEQ ID NO: 3 | 7290 | 19240 | 4150 | 4510 | 27420 | 11400 | 21810 |
| pTaq4 SEQ ID NO: 4 | 470 | 1050 | 1080 | 1570 | 5080 | 900 | 2360 |
| pTaq5 SEQ ID NO: 8 | ND | ND | 6060 | 4610 | 14190 | 3500 | 10700 |
| pTaq6 | 2486 | 7644 | ND | ND | ND | ND | ND |

ND = not determined
ON = overnight
+ = induction
− = no induction

Table I—Assay of thermostable DNA polymerase activity encoded by the various expression plasmids. Polymerase activity is interpreted as a reflection of gene expression and polymerase production.

The invention has been described in detail with particular reference to preferred embodiments thereof, but it will be understood that variations and modifications can be effected within the spirit and scope of the invention.

What is claimed is:

1. A gene for Taq polymerase wherein the sequence of the first thirty nucleotide bases in the native gene which code for the first ten amino acids in the mature native protein, has been changed A) by substituting therefor a modified nucleotide sequence selected from the group consisting of:
      SEQ ID NO: 2: ATG CGT GGT ATG CTG CCT CTG TTT GAG CCG AAG,
      SEQ ID NO: 4: ATG GAC TAC AAG GAC GAC GAT GAC AAG CGT GGT ATG CTG CCC CTC TTT GAC CCC AAG, or B) by inserting between the start codon (ATG) of the mature native protein and the codon, (AGG) for the second amino acid of the mature native protein, the sequence:
      SEQ ID NO: 8: GAC TAC AAG GAC GAC GAT GAC AAG.

2. The gene of claim 1, having a restriction site adjacent to and upstream from the start (ATG) codon, and the same restriction site adjacent to and downstream from the stop (TGA) codon.

3. The gene of claim 2 wherein the restriction sites are encoded by the nucleotide sequence GAATTC.

4. The gene of claim 1, wherein the native sequence:

SEQ ID NO: 1 ATG AGG GGG ATG CTG CCC CTC TTT GAG CCC PAG is altered to

SEQ ID NO: 2: ATG CGT GGT ATG CTG CCT CTG TTT GAG CCG AAG.

5. A method of increasing the production of Taq polymerase comprising the steps of:

A) providing a vector with a gene for Taq polymerase wherein the sequence of the first thirty nucleotide bases in the native gene which code for the first ten amino acids in the mature native protein, has been changed
   i) by substituting therefor a modified nucleotide sequence selected from the group consisting of:
      SEQ ID NO: 2: ATG CGT GGT ATG CTG CCT CTG TTT GAG CCG AAG,
      SEQ ID NO: 4: ATG GAC TAC AAG GAC GAC GAT GAC AAG CGT GGT ATG CTG CCC CTC TTT GAG CCC AAG, or
   ii) by inserting between the start codon (ATG) of the mature native protein and the codon, (AGG) for the second amino acid of the mature native protein, the sequence:
      SEQ ID NO: 8 GAC TAC AAG GAC GAC GAT GAC AAG, B) transfecting a compatible *E. coli* host with the vector of A) thereby obtaining transformed *E. coli* host cells; and C) culturing the transformed cells of B) under conditions for growth thereby producing Taq polymerase synthesized by the transformed host cells.

6. The method of claim 5 wherein the vector of step A has an inducible promotor.

7. The method of claim 5 wherein the production of Taq polymerase is induced with isopropyl-β-D-thiogalactoside (IPTG).

8. A vector with a gene encoding Taq polymerase wherein the sequence of the first thirty nucleotide bases in the native gene which code for the first ten amino acids in the mature native Taq polymerase has been changed A) by substituting therefor a modified nucleotide sequence selected from the group consisting of:
   SEQ ID NO: 2: ATG CGT GGT ATG CTG CCT CTG TTT GAG CCG AAG,
   SEQ ID NO: 4: ATG GAC TAC AAG GAC GAC GAT GAC AAG CGT GGT ATG CTG CCC CTC TTT GAG CCC AAG, or B) by inserting between the start codon (ATG) of the mature native protein and the codon, (AGG) for the second amino acid of the mature native protein, the sequence:
   SEQ ID NO: 8: GAC TAC AAG GAC GAC GAT CAC AAG, said vector having:
   i) selectable markers,
   ii) a suitable promoter, and
   iii) proper regulatory sequences for controlling gene expression.

9. An *E. coli* host cell comprising the vector of claim 8.

* * * * *

UNITED STATES PATENT AND TRADEMARK OFFICE
CERTIFICATE OF CORRECTION

PATENT NO. : 6,083,686  
DATED : July 4, 2000  
INVENTOR(S) : Mark A. Sullivan

Page 1 of 1

It is certified that error appears in the above-identified patent and that said Letters Patent is hereby corrected as shown below:

Column 23,
Line 67, should read: "GAG CCC AAG, or"

Column 25,
Line 3, should read: "TTT GAG CCC AAG is altered to"

Signed and Sealed this

Twentieth Day of November, 2001

Attest:

NICHOLAS P. GODICI
*Attesting Officer*    *Acting Director of the United States Patent and Trademark Office*